United States Patent [19]
Engel et al.

[11] Patent Number: 6,071,882
[45] Date of Patent: Jun. 6, 2000

[54] MEANS FOR TREATING PROSTATE HYPERTROPHY AND PROSTATE CANCER

[75] Inventors: Jürgen Engel, Alzenau; Thomas Reissmann; Hilde Riethmüller-Winzen, both of Frankfurt am Main; Jürgen Rawert, Alzenau, all of Germany

[73] Assignee: ASTA Medica AG, Dresden, Germany

[21] Appl. No.: 09/062,704

[22] Filed: Apr. 20, 1998

Related U.S. Application Data

[62] Division of application No. 08/908,198, Aug. 7, 1997
[60] Provisional application No. 60/025,990, Sep. 12, 1996, and provisional application No. 60/043,228, Apr. 10, 1997.

[51] Int. Cl.⁷ .................. A61K 38/00; A61K 31/495; A61K 31/50; A61K 31/18
[52] U.S. Cl. .................. 514/15; 514/254; 514/255; 514/603
[58] Field of Search .................. 514/255, 15, 254, 514/603

[56] References Cited

FOREIGN PATENT DOCUMENTS

401653 A2  12/1990  European Pat. Off. .............. 514/255
2 218 335  11/1989  United Kingdom .

OTHER PUBLICATIONS

Mori et al., Yakuri to Chiryo, 20(2), 375–81 Abstract Only, 1992.

*Primary Examiner*—Jerome D. Goldberg
*Attorney, Agent, or Firm*—Pillsbury Madison & Sutro LLP

[57] ABSTRACT

A regime for therapeutic management of a benign prostatic hyperplasia and prostatic cancer employs Cetrorelix alone or in combination with α-reductase inhibitors or α-receptor blocking agents. The regimen reduces the volume of the prostate and avoids the side effects associated with testosterone levels being in a castration range. Cetrorelix is administered at dosages between 0.5 mg/day and 20 mg/week or about 0.014 mg/kg body weight per day to 0.30 mg/kg body weight per week or at levels of about 25 to 120 mg of Cetrorelix per month or 0.376 mg/kg to 1.71 mg/kg per month. Cetrorelix can be administered with α-reductase inhibitors or α-receptor blocking agents.

12 Claims, 4 Drawing Sheets

Fig. 1

CETRORELIX
DEVELOPMENT INDICATION BPH

| INDICATION | SUBJ. NOS. | RESULT | PHASE | SALT* | DOSE / DAY (mg) | POSOLOGY (days) |
|---|---|---|---|---|---|---|
| BPH | 11/11 | Relief of symptoms<br>Decrease of prostate volume<br>No castration | I / II a | 1 | 0.5 bid | 28 |
| BPH | 7/7<br>7/7 | Relief of symptoms<br>Decrease of prostate volume<br>independent from extent of hormonal suppression | I / II a | 1<br>2 | 10(d1)+ 1 (d2–28)<br>30(d1)+30(d8) | 28<br>28 |
| BPH (not operable) | 15/10 | | II | 1 | 5bid(d1+2)+<br>1od (d2.56) | 56 |
| BPH | 84/78 (79)<br>/27<br>/25<br>/26 | Obj.: ↓ IPSS<br>↓ prostate volume<br>↓ hormones, including DHT<br>dose dependent efficasy<br>castration level not necessary<br>long lasting effect ≥ 3 months after treatment termination | II | 1 | Pla run-in<br>10(d8-13)+1(d-35)<br>1 (d8-35)<br>Pla(d8-35) | 28 +<br>7d Pla run-in |
| SUM FINISH | 114 pat. | | | | | |

\* 1 = CETRORELIX ACETATE (Lyophilisate)
2 = CETRORELIX PAMOATE

PROSTATE SIZE – MEANS

PROSTATE SIZE – MEAN ABSOLUTE CHANGES FROM BASELINE

RATE OF PATIENTS WITH AN I-PSS IMPROVEMENT ≥ 40%
PER PROTOCOL ANALYSIS
CETRORELIX ACETATE

| TREATMENT | | ≥ 40 % RESP. | | ≥ 30 % RESP. |
|---|---|---|---|---|
| | | PT. NO. | PT. % | % PT. |
| PLA | NO | 18 | | |
| | YES | 17 | 28 | 32 |
| C01 | NO | 14 | | |
| | YES | 11 | 44 | 52 |
| C10 | NO | 14 | | |
| | YES | 12 | 46 | 53.8 |

IMPROVEMENT OF MAXIMUM UROFLOW ≥ 3 ml/sec
AT END OF TREATMENT PHASE
PER PROTOCOL ANALYSIS

| | IMPROVEMENT ≥ 3 ml/sec | | | | | |
|---|---|---|---|---|---|---|
| | NO | | YES | | TOTAL | |
| TREATMENT | NO. | % | NO. | % | NO. | % |
| PLA | 13 | 52.0 | 12 | 48.0 | 25 | 100.0 |
| C01 | 12 | 48.0 | 13 | 52.0 | 25 | 100.0 |
| C10 | 16 | 61.5 | 10 | 38.5 | 26 | 100.0 |

MEANS FOR TREATING PROSTATE HYPERTROPHY AND PROSTATE CANCER

This application is a Division of Ser. No. 08/908,198 filed Aug. 7, 1997. This application claims the benefit of U.S. Provisional Applications Ser. No. 60/025,990, filed Sep. 12, 1996 and 60/043,228, filed Apr. 10, 1997.

BACKGROUND OF THE INVENTION

1. Field of the Invention

The invention is related to a method of treating benign prostate hypertrophy (BPH) and prostate cancer as well as to means of use therefor.

2. Description of Related Art

BPH is a disease conditioned by age and affects approximately 60% of all men older than 60. Pathogenetically, an elevated accumulation of dihydrotestosterone in the prostate tissue is assumed to cause enlargement of the prostate. The accumulation of dihydrotestosterone is thought to be the result of elevated intracellular bonding based on receptor increase. The increase in receptors is stimulated by the elevation of the estrogen levels relative to androgen levels which decrease with age. The urological symptoms consist in an elevated frequency of miction due to elevated residual urine, which bothers the patients especially during the night hours. This is accompanied by a weak flow of urine, a time-delayed start of miction, and repeated infections of the bladder and kidneys.

Surgical elimination of the obstruction due to prostate enlargement is still considered the "gold standard" within the various modalities of treatment. Surgery, however, is not effective for all patients. Open operation or a transurethral resection results in no improvement in approximately 10 to 15% of the patients due to the presence of other causes, e.g. neurogenic bladder, infections. In addition, these invasive methods entail additional risks such as the occurrence of a retrograde ejaculation, diminished libido and urine incontinence. Less invasive methods exist, e.g. balloon dilatation and treatment with hyperthermia or microwaves.

It has been established that an androgen-ablative therapy can yield positive results in the case of BPH; however, it is unclear whether full suppression should be achieved. The standard therapy for testosterone suppression in the case of prostate carcinomas consists in a bilateral orchiectomy. This is not generally acceptable for a benign sickness such as BPH. Another possibility involves influencing the effects of the sexual steroids through the use of LHRH analogues (LHRH luteinizing hormone-releasing hormone).

After an initial stimulation of the steroid, the use of "superagonists" causes suppression of testosterone at castration levels. The stimulation is due to their mechanism of action. Unfortunately, the use of "superagonists" has the same undesirable side effects associated with surgical castration.

Dyssynergia α-receptor blockers can be used in the case of a rigid sphincter or bladder sphincter. Alternative drug regimens involve the use of 5-α-reductase inhibitors such as Finasteride to inhibit the formation of dihydrotestosterone. This regimen has the additional advantage of not negatively influencing the libido or potency.

EP 0.401,653 teaches the use of Naftopidil for therapy of dysuria in BPH (oral daily 10–100 mg). Dysuria is discussed in the background section.

WO publication 91/100731 describes a combination therapy for the prophylaxis or treatment of BPH by the combined administration of 2 or more therapeutic substances. The substances are selected from the group of 5-α-reductase inhibitors, anti-estrogens, aromatase inhibitors, inhibitors of 17β-hydroxysteroid dehydrogenase activity and, in a few instances, of anti-androgens and/or LHRH agonists/antagonists. The anti-androgens were preferably given 2 to 4 hours before the administration of the LHRH agonist.

WO publication 91/00733 teaches the treatment of androgen-dependent diseases with a new anti-androgen which can also be used in the context of a combination therapy. The treatment includes the steps of inhibiting the testicular hormonal secretion by administering an antagonist of LHRH or an agonist of LHRH along with a pharmaceutically effective amount of an anti-androgen.

WO publication 92/16233 describes the combined use of an inhibitor of 5-α-reductase and an anti-androgen for the treatment of prostate cancer. The combination of Finasteride with an anti-androgen, e.g. Flutamide, is also taught. The use of a composition of various LHRH agonists and of an anti-androgen for treating BPH is also suggested by U.S. Pat. No. 4,472,382.

WO publication 92/16213 teaches a method of treating BPH by administering an inhibitor of 5-α-reductase select from 17β-substituted 4-azasteroid, 17β-substituted non-azasteroid, 17β-acetyl-3-carboxy-androst-3,6-diene together with an $\alpha^1$ adrenergic receptor blocker selected from Terazosin, Doxazosin, Prazosin, Bunazosin, Indoramin, Alfuzosin.

The use of the LHRH antagonist Cetrorelix (SB 75), (see also EP 0299 402), for treating BPH is suggested in "The Prostate" 24:84 92 (1994), (Gonzalez-Barcena et al). Gonzalez-Barcena et al. report desirable clinical results, e.g. a decrease in prostate volume, after the administration of 500 μg Cetrorelix (SB-075) every 12 hours for 4 weeks to BPH patients. Prostate carcinoma patients were also similarly treated for 6 weeks. In all patients, there was initially a lowering in testosterone levels to a castration level. In the BPH patients, the testosterone levels fluctuated at subnormal levels. None of the patients had testosterone levels which reached castration values during the last three weeks of the treatment. There was a distinct decrease of the symptoms of dysuria and also the prostate volume. In the prostate carcinoma patients, the testosterone values were measured again at the castration levels at the end of the 6 weeks of therapy along with a considerable improvement in the overall condition of the patient.

The potential suitability of LHRH antagonists, including Cetrorelix, for treating BPH appears in a review article appearing in Arch.-Pharmakol. 350, Suppl., R16, 1994 (Romeis, Ochs, Borbe). In vitro bonding of Cetrorelix to LHRH receptors on the pituitary gland of swine is mentioned. Also mentioned are other possible clinical areas of application, including hormone-dependent tumors.

A comparative survey of the endocrine therapy of BPH in conjunction with 5-α-reductase inhibitors, aromatase inhibitors and anti-androgens is presented in Urology, 1994, 43, 22 suppl. (7–16). However, only LHRH agonists are described.

An overriding disadvantage of known preparations and methods is that the patient usually experiences a sharp drop in testosterone levels along with its associated side effects. In addition, known preparations have only a relatively short term effect. The prostate volume rises once administration stops. An effective therapy scheme for the treatment of BPH with Cetrorelix has not been established.

SUMMARY OF THE INVENTION

The disclosed invention is directed to a long-lasting therapeutic agent having few side effects for the treatment of both BPH and prostate cancer.

The problems existing with the treatments described above are solved by administering the LHRH antagonist Cetrorelix alone or in combination with α-blockers or 5-α-reductase inhibitors such as Finasterides. Preferably, Cetrorelix was administered intermittently according to a specified therapy scheme.

It is also possible with the LHRH antagonist Cetrorelix to determine the extent of a testosterone suppression via the level of the applied dose and also to compensate for it.

BRIEF DESCRIPTION OF THE DRAWINGS

FIG. 1 is a summary of the clinical results for specific Cetrorelix dosage regimens. PLA refers to a placebo;

TREATMENTS: C01 refers to a dosage regimen of 1 mg/day s.c. for 28 days and a 3 months follow-up observation period. C10 refers to a dosage regimen of 10 mg/day for the first one to five days followed by a dosage regime of 1 mg/day s.c. for 28 days and a 3 months follow-up observation period.

Figure 2A:
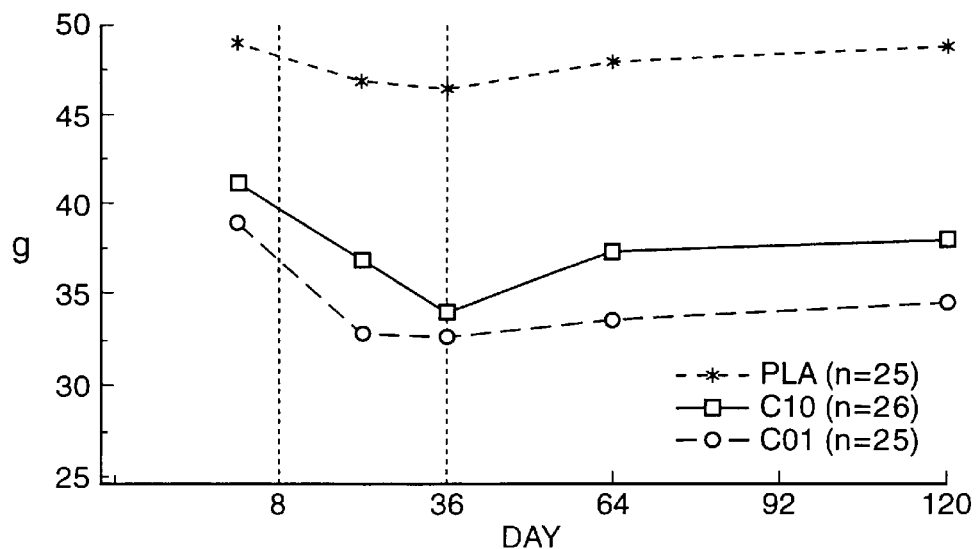
FIG. 2 (a) shows the effect of the C01 and C10 treatments on prostate size. PLA refers to a placebo.
Figure 2B:
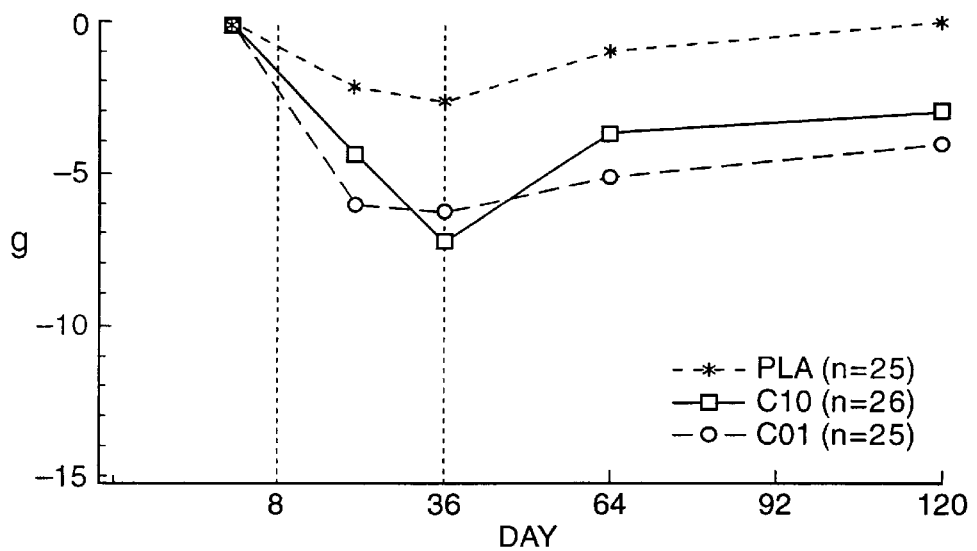
Figures 4A, 4B:
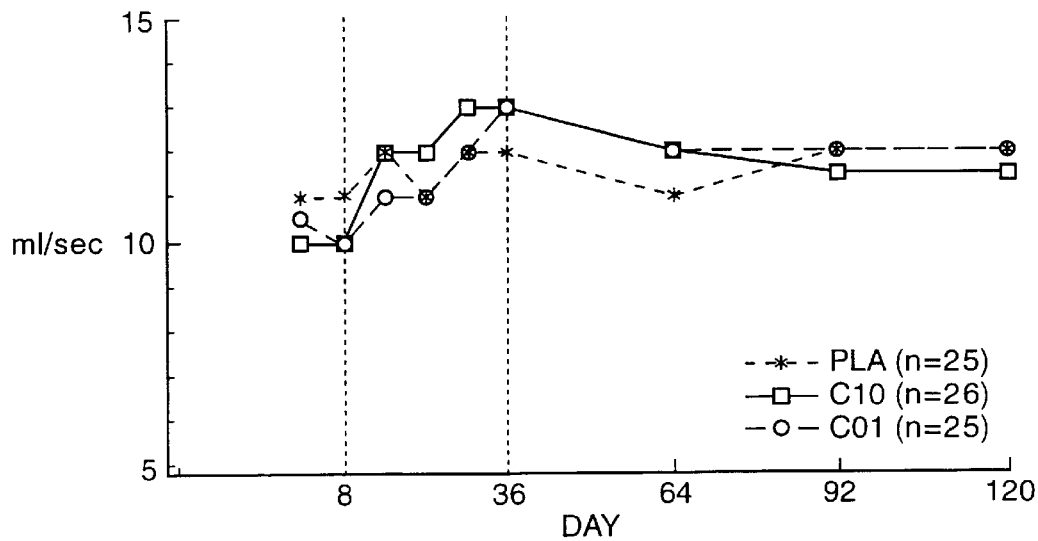

FIG. 2 (b) illustrates the absolute changes in prostate size from baseline for the C01 and C10;

FIG. 3 (a) shows the number of patients with an I-PSS improvement ≧40% and also with an improvement ≧30% resulting from the treatment C01 and C10 (defined above). PLA is the placebo. I-PSS (International Prostate Symptom Score) includes the following indicia of 1) feeling of incomplete voiding, 2) increased frequency of voiding, 3) dribbling, 4) difficulties to postpone voiding 5) weak urinary stream 6) increased effort to start voiding and 7) nycturia;

FIG. 3 (b) shows the I-PSS improvement with the C10 and C01 treatments (defined above) over 120 days, including the observational follow-up period;

FIG. 4 (a) shows the improvement in maximum uroflow ≧3 ml/sec C10 and C01 (defined above) treatment phases. PLA is the placebo; and FIG. 4 (b) shows the rate of uroflow as a function of the C01 and C10 treatments (defined above) over a 120 day period.

DESCRIPTION OF THE PREFERRED EMBODIMENTS

The invention will be explained in detail using the following clinical results:

Examples

Example 1

Cetrorelix is administered in a dose of 0.5 mg to 2 mg daily for 4 to 8 weeks for the therapy of BPH. A dose of 5 mg to 30 mg, dispensed once per week or every 10 days also over a time period of 4 to 8 weeks as well as one every two weeks or one injection per month of 20 mg to 60 mg can also decisively improve the clinical symptoms and signs. Submaximal decreases of testosterone occur, but these are above those levels associated with castration. The prostate volume decreases by 20 to 40% during the treatment time of 4 to 8 weeks. An increase of the peak flow of approximately 3 ml/sec of the urine, comparable to the α-blockers, is also achieved with this therapy regimen. In addition, at least 30% of the patients achieve an improvement of the urine flow of 6 ml/sec with this therapy. This is almost equivalent to an improvement like that associated with the golden standard operation, and in considerably shorter time. No limitations in sexual performance are observed. There are also significant improvements as regards quality of life. These clinical benefits continue for at least 3 to 6 months after therapy. This allows a long-term therapy of BPH with only an intermittent treatment of 2 to max. 4 injection cycles over 4 to 8 weeks.

This therapy represents a significant therapeutic advance in the treatment of BPH since it not only achieves an improvement of the clinical symptoms of BPH but also a diminution of the prostate and an improvement of the urine flow like those associated with surgery. The protocols of the invention avoid the negative consequences of an operation, e.g. urine incontinence, retrograde ejaculation, blood loss with the consequence of blood transfusions and also the risks of infection associated with surgery.

Example 2

Cetrorelix is administered with α-reductase inhibitors or α-receptor blocking agents to a patient as follows:

For 1 to 12 weeks, Cetrorelix is administered to the patient followed by a 1–12 week period where an α-reductase inhibitor of 5 mg/day, an α-receptor blocking agent in the dose range of 2 mg to 10 mg/day or of 0.1 mg to 0.4 mg/day dependent on each agent or a drug of natural origin 1–6 capsules or tablets/day used for the treatment of BPH is administered. Alternatively, Cetrorelix can be administered for a 1 to 12 weeks period followed by retreatment with Cetrorelix after one to six months.

In summary, it can be readily seen that treatment of BPH with a specific therapy regime involving Cetrorelix or especially a combination of Cetrorelix with 5α-reductase inhibitors or α-blockers such as Naftopidil has decided benefits which occur quickly and are long-lasting.

An effective and economic therapy of this widespread disease can be achieved therewith, which is of extraordinary social and economic significance.

We claim:

1. A regime for therapeutic management of benign prostatic hyperplasia in a mammalian organism without testosterone levels being in castration range comprising the administration of an effective synergistic amount of LH-RH antagonist Cetrorelix in combination with α-receptor blocking agents according to a regime wherein Cetrorelix is administered over time and in a dosage amount sufficient to reduce the volume of the prostrate, BPH symtoms and/or prostate specific antigen levels, without the side effects associated with testosterone levels being in a castration range.

2. The regime according to claim 1 which involves the administration of Cetrorelix at dosages between 0.5 mg/day and 20 mg/week or about 0.007 mg/kg body weight per day to 0.30 mg/kg body weight per week.

3. The regime according to claim 1 wherein the dosage amount is at levels of about 20 to 120 mg of Cetrorelix per month or about 0.285 mg/kg to 1.71 mg/kg per month for one to six months.

4. The treatment according to claim 1 or 3 wherein Cetrorelix is administered with α-receptor blocking agents in a specific timely regime.

5. The treatment according to claim 1 or 3 wherein the timely regime is as follows:

1 to 12 weeks of Cetrorelix treatment followed by 1 to 12 weeks of treatment with an α-receptor blocking agent.

6. The treatment according to claim 5 wherein the regime is as follows:

1 to 12 weeks of Cetrorelix treatment followed by 1–12 weeks treatment with an α-receptor blocking agent used for the treatment of BPH; or alternatively, 1–12 weeks of Cetrorelix treatment followed by continuous treatment with an α-receptor blocking agent and retreatment with Cetrorelix after six months.

7. The regime according to claim 1 comprising the administration of about 0.5 to 5 mg per day Cetrorelix for 1 to 12 weeks continuously or intermittently, together with an α-receptor blocking agent, optionally followed by retreatment with Cetrorelix alone or with an α-receptor blocking agent after 6 months.

8. The regime according to claim 1 wherein the α-receptor blocking agent is a uroselective α-1 adrenoceptor blocking agent.

9. The regime according to claim 8 wherein the uroselective α-1 adrenoceptor blocking agent is selected from the group consisting of Naftopidil, Terazosin, Doxazosin and Tamsulosin.

10. The regime according to claim 9 wherein the uroselective α-1 adrenoceptor blocking agent is administered in a daily dosage of 2 mg to 10 mg.

11. The regime according to claim 1 wherein the α-receptor blocking agent is Naftopidil.

12. The regime according to claim 3 wherein the dosage amount is at levels abour 20 to 120 mg Cetrorelix per month or about 0.285 mg/kg to 1.71 mg/kg per month for one to three months.

* * * * *

UNITED STATES PATENT AND TRADEMARK OFFICE
CERTIFICATE OF CORRECTION

PATENT NO. : 6,071,882
DATED : June 6, 2000
INVENTOR(S) : Engel et al.

It is certified that error appears in the above-identified patent and that said Letters Patent is hereby corrected as shown below:

Title page,
The title should read: -- MEANS FOR TREATING PROSTATE HYPERPLASIA AND PROSTATE CANCER -- (instead of ......HYPERTROPHY...)

Column 2,
Line 23, -- select<u>ed</u> -- instead of "select"

Column 3,
Line 5, -- <u>is</u> administered -- instead of "was administered"
Line 21, -- ... for <u>23</u> days... -- instead of "....28 days..."

Figures 3A, 3B:
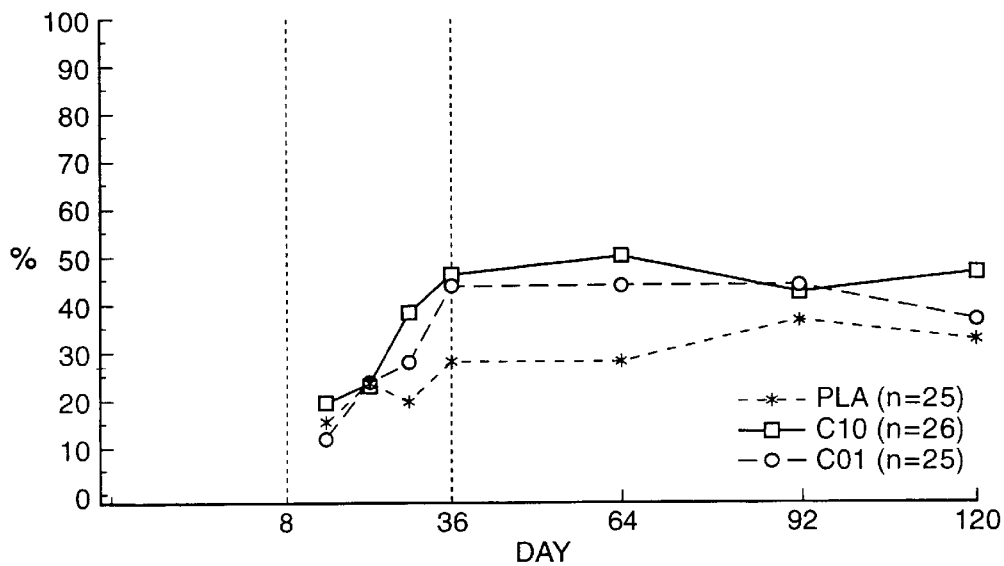

Drawings,
Fig. 1, line 14, -- 10(d8-13) + 1(d<u>14</u>-35) instead of "...d-35...) )
Fig. 1, line 16, -- effica<u>c</u>y -- instead of "efficasy"
Fig. 3(a), line 1, please add: "and ≥30%" to read, -- Rate of Patients with an I-PSS Improvement ≥40% <u>and ≥30%</u> --

Signed and Sealed this

Ninth Day of April, 2002

Attest:

JAMES E. ROGAN
Attesting Officer     Director of the United States Patent and Trademark Office